(12) United States Patent
Tavares

(10) Patent No.: US 6,683,031 B1
(45) Date of Patent: Jan. 27, 2004

(54) ROPE HANDLING SYSTEM

(75) Inventor: Bruce A. Tavares, Hartland, WI (US)

(73) Assignee: React, LLC of Delafield, Delafield, WI (US)

( * ) Notice: Subject to any disclaimer, the term of this patent is extended or adjusted under 35 U.S.C. 154(b) by 0 days.

(21) Appl. No.: 10/229,452

(22) Filed: Aug. 28, 2002

Related U.S. Application Data

(63) Continuation-in-part of application No. 09/861,842, filed on May 21, 2001, now Pat. No. 6,506,712.

(51) Int. Cl.⁷ .................. C10M 159/00; C08B 11/20
(52) U.S. Cl. .................. 508/216; 8/116.1; 204/157.68; 536/85; 57/1 R
(58) Field of Search .............................. 57/1 R; 508/216

(56) References Cited

U.S. PATENT DOCUMENTS

| | | | |
|---|---|---|---|
| 3,108,890 A | 10/1963 | Beaver et al. | 204/157.63 |
| 3,502,426 A | 3/1970 | Krassig et al. | 8/116.1 |
| 3,704,578 A * | 12/1972 | Myers | 57/1 R |
| 3,846,521 A | 11/1974 | Osterholtz | 264/22 |
| 3,926,555 A * | 12/1975 | Reine et al. | 8/189 |
| 3,962,054 A | 6/1976 | Wattiez et al. | 204/159.12 |
| 4,051,306 A | 9/1977 | Tobias et al. | 526/1 |
| 4,063,885 A * | 12/1977 | Mares et al. | 8/115.7 |
| 4,190,623 A | 2/1980 | Bobeth et al. | 264/22 |
| 4,316,982 A | 2/1982 | Holst et al. | 536/88 |
| 4,486,585 A | 12/1984 | Turunen et al. | 536/30 |
| 4,654,379 A | 3/1987 | Lapin | 522/15 |
| 4,896,400 A * | 1/1990 | Polli | 19/0.27 |
| 5,333,442 A * | 8/1994 | Berger | 57/314 |
| 5,710,274 A | 1/1998 | Yuan et al. | 544/375 |
| 5,719,274 A | 2/1998 | Doenges et al. | 536/85 |
| 5,837,009 A * | 11/1998 | Valkanas | 8/125 |
| 5,928,709 A | 7/1999 | Doenges et al. | 427/2.14 |
| 6,354,067 B2 * | 3/2002 | Foil, Jr. | 57/1 R |
| 6,506,712 B2 * | 1/2003 | Tavares | 508/216 |

OTHER PUBLICATIONS

"Electron Processing Technology: A Promising Application for the Viscose Industry", presented at the 10$^{th}$ International Meeting on radiation Processing, May 11–16, 1997, Anaheim, CA.

* cited by examiner

*Primary Examiner*—Ellen M. McAvoy
(74) *Attorney, Agent, or Firm*—Alfred D Lobo

(57) ABSTRACT

A method is provided for preparing a multifunctional additive involving irradiating raw cotton plant material with an electron beam source, continually blending the raw cotton plant material during the irradiating and micronizing the irradiated cotton plant material. The invention is improved wherein the irradiating and blending of the raw cotton plant material is performed while the raw cotton plant material is in rope form. Irradiated rope is suitably tensioned before micronizing to compensate for degradability of the rope incurred during irradiation.

12 Claims, 1 Drawing Sheet

ROPE HANDLING SYSTEM

CROSS-REFERENCE TO RELATED APPLICATIONS

This application is a continuation-in-part application based on U.S. patent application Ser. No. 09/861,842 filed May 21, 2001 now U.S. Pat. No. 6,506,712.

FIELD OF THE INVENTION

The present invention relates to multifunctional additives and methods for preparing and using the same. Specifically, multifunctional additives are produced by irradiating and subsequently fragmenting, or micronizing, plant materials, such as raw cotton. A multifunctional additive made in accordance with the method of the present invention has the following attributes: (1) anti-misting properties, (2) low coefficient of friction, (3) is suitable for use as a substitute for talc, as for example in cosmetics and other personal care products, and (4) is suitable as a substitute for asbestos in industrial applications.

BACKGROUND OF THE INVENTION

Radiation processing for modification and enhancement of polymeric material properties has been well documented in the prior art. In particular, electron beam processing has been used to improve thermal, chemical, barrier, impact, wear, and other properties of many inexpensive materials extending their utility to demanding applications typically dominated by higher cost materials. Electron beam processing may result in cross-linking, degradation, or a combination of the two, depending on the nature of the polymeric materials and the dosage of radiation applied. Results of electron beam processing of cross-linkable plastics has yielded materials with improved dimensional stability, reduced stress cracking, higher service temperatures, reduced solvent and water permeability. More specifically, radiation induced cross-linking in polyethylene has resulted in increased modulus, tensile and impact strength, hardness, deflection and service temperature stress/crack resistance, abrasion resistance, creep and fatigue resistance. In contrast, radiation processing can also induce degradative, or scissioning, effects in polymeric materials such as polytetrafluoroethylene (PTFE). Scrap or off-spec PTFE, degraded by electron beam processing, has been identified as useful in the production of abrasion-reducing additives.

PTFE has found a use as a friction-reducing additive in many areas, including the printing ink industry. PTFE additives provide ink formulations with anti-rub properties so that the inks are resistant to smearing and marring. However, PTFE cost is relatively high in comparison to other anti-abrasion additives and therefore PTFE use is often cost prohibitive.

Radiation processing has also been used in degrading high molecular weight cellulose ethers common polymeric materials into low molecular weight cellulose ethers producing low molecular weight cellulose ethers for varying uses. For example, U.S. Pat. No. 5,928,709 to Doenges et al. discloses a method of producing low molecular weight cellulose ethers by irradiation of a mixture of higher molecular weight cellulose ethers and an Arrhenius and/or Bronsted base. The resulting low molecular weight cellulose ethers are suitable as water-binding agents, thickeners and emulsion stabilizes.

Clays and talcs have also found traditional use in the reduction of friction. For instance, clays are currently used in down hole drilling fluids useful in reducing friction during drilling operations. Debris present in a down hole is cleared by pumping clay into the bore hole where the clay lowers the viscosity of the debris and aids in moving the clay to an exit. Ideally, the clay maintains the debris in a suspended mixture without building viscosity. In practice, a significant buildup in viscosity is experienced in this process and the efficiency of clearing debris from down holes using clay is significantly less than desired. The cost of suitable clays may also be prohibitive.

Talc has found wide use as a friction-reducer in personal care products, most notably mascaras and body powders. Although hypoallergenic in nature and therefore safe for contact with the human body, talc suitable for personal care products is expensive to manufacture.

The above-described background highlights the need for multifunctional additives with improved low COF characteristics obtainable at a reduced cost. Such additives should not only be economical to manufacture, but also derived from a cheap but plentiful raw material source. The method of manufacture should also be flexible to accommodate production of additives suitable for a variety of applications.

SUMMARY OF THE INVENTION

The invention relates to a method for preparing a multi-functional additive from a raw plant material and, in particular, cotton. The raw plant material is irradiated with an electron beam source to form an irradiated product. During the irradiation, the raw plant material is continually blended to provide a uniform radiation dosage to the raw plant material. Following irradiation, the irradiated product is fragmented, or micronized, to form the additive having an average diameter size less than that of the original raw plant material starting product.

In the preferred embodiment of the invention, the method utilizes raw cotton as the raw plant material.

Prior to the irradiating step of the invention, a granulating step may be included wherein the raw plant material is granulated to reduce the diameter size of the raw plant material before irradiating. In one approach to the invention, the granulating step may reduce the raw plant material to about a ⅛ inch to about a ¼ inch diameter size prior to the irradiating step.

The irradiation step of the invention utilizes an electron beam source for delivering accelerated electrons to the raw plant material. A suitable dosage may be between about 30 megaRads to about 100 megaRads depending upon the particular application the resulting additive will be used in. A dosage of about 80 megaRads to about 100 megaRads is preferable where the additive will be used in friction-reducing applications. However, the total dosage is preferably administered in multiple low dosage passes.

The micronizing step of the invention is meant to reduce the size of the irradiated product and may be carried out with a jet classifying mill. The micronizing step is intended to reduce the average diameter size of the irradiated plant material to an average diameter size of about 3 microns to 4 microns with 99% of the average diameter sizes being below 10 microns.

In addition to a preparatory method, the invention is also directed to an additive, useful in reducing friction, providing anti-misting properties, and suitable as a substitute for talc and asbestos, produced from a raw plant material having been subjected to irradiation by an electron beam. During irradiation, the raw plant material is continually blended so that the raw plant material receives a uniform dosage of irradiation. The irradiated product is subsequently micronized to form an additive with a reduced diameter. The raw plant material used to product the additive is preferably raw cotton.

An additive according to the invention as described above is useful in reducing the coefficient of friction of a substance and may be mixed with the substance in a sufficient amount to effectively reduce the coefficient of friction of the substance/additive mixture. The substance may be a lubricant/grease, cosmetic formulation, or matting agent.

The invention further contemplates taking irradiated raw cotton plant material in rope form and feeding same through an idler compensating unit, an uncoiling and tensioning unit, a slack control unit and a cotton pinch roll feed unit. The irradiated rope product is then micronized as previously described.

After being micronized into powdered form, the irradiated rope is washed, agitated and dried so that the powdered cotton has a pH of 7.0.

Various other features, objects and advantages of the invention will be made apparent from the following description taken together with the drawings.

BRIEF DESCRIPTION OF THE DRAWINGS

The drawings illustrate the best mode presently contemplated in carrying out the invention.

In the drawings.

DETAILED DESCRIPTION OF THE INVENTION

Figure 1:
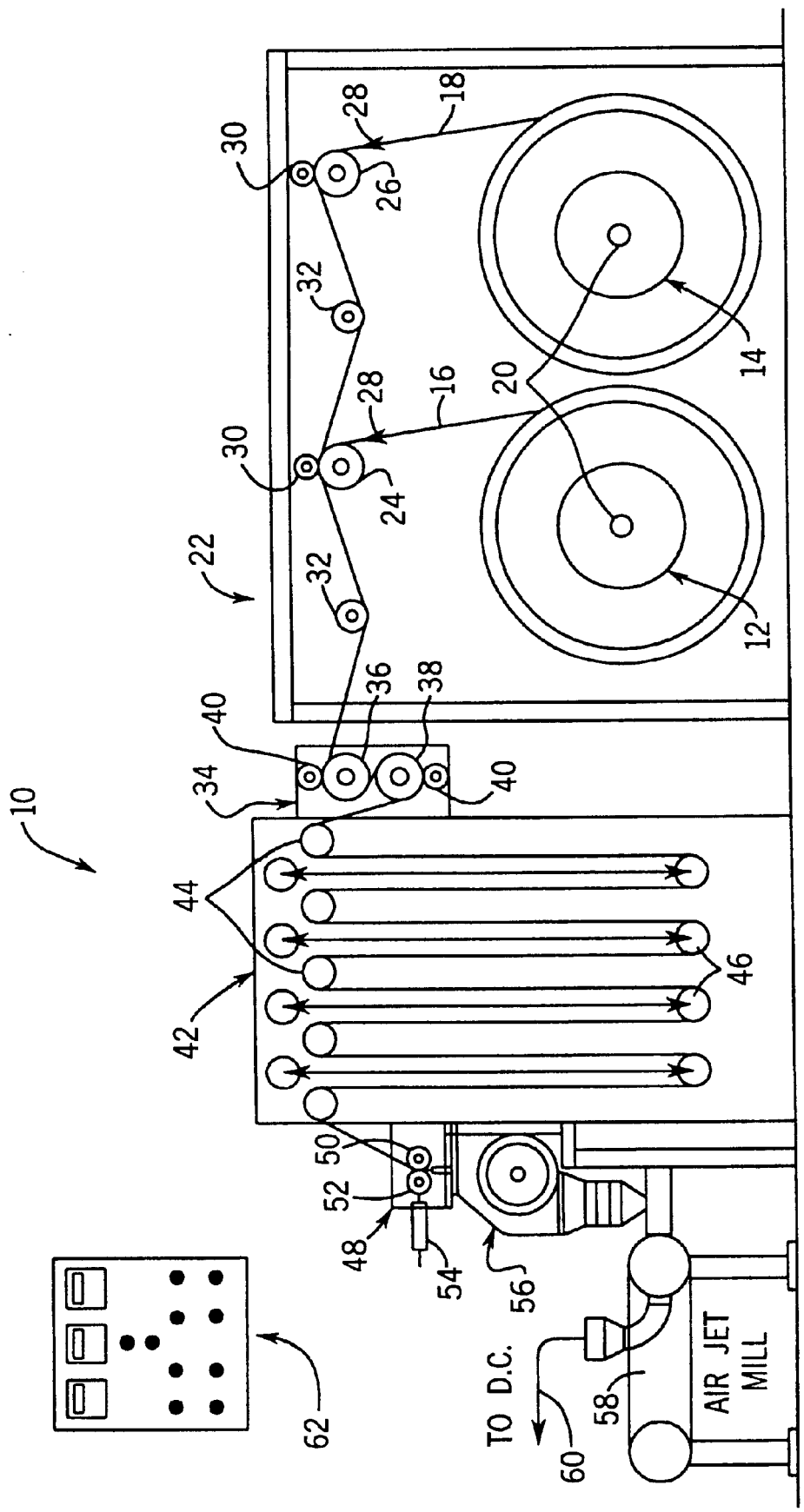
FIG. 1 is a side view of a rope handling system in accordance with the invention.

The preferable raw plant material is raw cotton, possibly brought into the process in a baled form subsequent to harvest activities. Cotton is particularly desirable because no pretreatments of starting materials are necessary and raw natural products may be brought directly from their original source (e.g., harvest from a field) into the process, therefore reducing costly pretreatment steps such as etherification.

Cotton is a particularly attractive raw plant material for the invention as cotton is grown in about 80 countries, in a band that stretches around the world between latitudes 45° N to 30° S. After planting, seedlings appear five days later, with the first flower buds appearing after approximately six weeks. In another three to five weeks, these buds become flowers. The flowers are short lived and fall from the cotton plant, leaving behind a small seed pod, known as the boll. Each boll contains about 30 seeds, and up to 500,000 fibers of cotton. Each fiber grows its full length in three weeks and for the following four to seven weeks, each fiber gets thicker as layers of cellulose build up cell walls. Approximately ten weeks after flowering, the boll splits open and the raw cotton fibers are exposed to sunlight. As the fibers lose water and die, each fiber collapses into a twisted ribbon structure. Cotton is then picked by hand or by cotton harvesters. Cotton fibers are separated from the associated cotton seeds in a process called ginning. Following ginning, the cotton fiber is pressed into bales and wrapped for protection.

Prior to processing the raw cotton through the method according to the invention, the raw cotton fibers are debated, thus allowing the cotton fibers to be stretched into a thin sheet. The unbaled cotton sheet is cut or chopped into fairly small pieces, for example, about 2"×2" in size. The cut pieces are then fed into a pelletizer or a compressor and compressed into pellets of about ½" in size.

Alternately, if palletizing is not acceptable, the cut pieces may be chopped to form small squares in the range of ½" to ¼" in size. Chopping may be performed in a HOG or Cumberland chopper or similar equipment.

Thereafter, it is preferred to expose the raw cotton material to irradiation with electrons when the raw material is in a relatively dry state. Preferably, the raw material will have a water content of less than about 0.05% to 1.0% by weight of the raw material.

Various sources of radiation may be utilized with the process according to the invention. Useful sources of radiation may be either continuous or pulsed electron beam accelerators currently available in the art. In general, any accelerator from the main types including electrostatic direct-current, electrodynamic DC, radio frequency linear accelerator, magnetic-induction LINACs and continuous wave machines may be used in the process. The dosage, or amount of energy absorbed, is measured in units of mega-Rads (MR or Mrad), where one MR is equal to one million ergs per gram, or kilograys (kGy), where one kGy is equal to one thousand joules per kilogram. The energy dose delivered to the raw material in the method is 30 to 100 MR. Preferably, dosages on the high end of that spectrum, 80 to 100 MR are preferred where the resulting irradiated materials will be used as anti-friction additives.

In accordance with the presently preferred embodiment of the subject invention, the radiation is produced by an electron accelerator. The electron beam is applied through a window to the pellets or small chopped pieces of cotton being carried on a tray system where the material is blended or turned after each pass through the beam window. The irradiation and blending may also be carried out in a ribbon type blender with the radiation applied through a beam window or with a beam horn. In a typical electron accelerator, a dosage of 2.5 MR is applied per pass of the product past the beam window. If the radiation dose is higher, the cotton may burn or degrade. Thus, with a total dosage of 80 MR, the material must be passed under the accelerator window thirty-two times. After each pass, the material must be turned over or blended before again being exposed to the radiation.

In contrast, a process according to the invention avoids the limitations in prior art techniques by providing for the raw plant material to be continually blended during the irradiating step. Multi-pass radiation with the material being turned or blended between each pass results in uniform radiation of the raw cotton.

Irradiation of the raw plant material forms an irradiated product which is subsequently guided to a micronizing step. Micronizing of the irradiated product is carried out by a micronizing mill, preferably a jet classifying mill such as a model 30 Roto-Jet manufactured by Fluid Energy Al-Jet Company. The jet mill is operated using an air flow of 1500–2000 CFM at 120 psi. This is a high speed grinding mill with an integral, independently driven dynamic classifier producing a narrow size distribution. Although size of the micronized irradiated product may vary depending on the ultimate application for the additive, the general particle range is from about 2 microns to about 10 microns for the applications disclosed herein. For friction-reducing additive applications, 99% of the particles will be below 10 microns in average diameter size with a minimal number of additive particles less than 2 microns in diameter and 0% below 1.0 micron. An average particle diameter of 3 to 4 microns is desirable for friction-reducing applications.

It has been discovered that in the process of carrying out the irradiation process described above that the manual debating and cutting of the raw cotton fibers and manual placing of the cut fibers into a tray before further chopping or pellitizing is extremely labor intensive. In addition, if the raw cotton segments are not constantly rotated, they burn.

In order to provide an improved system which overcomes the above noted drawbacks and enables a greater throughput, the raw cotton fibers are roped and then irradiated. The irradiated rope is then fed through various roller and tensioning structure before being micronized.

Referring now to FIG. 1, thereshown is a rope handling system 10 constructed in accordance with the present invention. The rope handling system 10 includes at least one and preferably a pair of spools 12 of rope coils 16, 18, respectively, fabricated of raw cotton and irradiated according to the process described above. The spools 12, 14 or rope uncoiler units have non-driven shafts 20 rotatable in bearings (not shown). The height of each shaft 20 is such that the rope coil 16, 18 can be slid onto the shaft 20 from a pallet jack (not shown). Incorporated into the shaft assembly, between the bearings is a mechanical braking system (not shown) to prevent the rope coil 16, 18 from freewheeling and overfeeding the rope. The rope handling system 10 is designed to handle rope diameters typically in the ⅜ inch to ⅝ inch range. Each spool 12, 14 has the capacity for holding 1,000–50,000 feet of irradiated cotton rope thereon and is generally uncoiled at a rate of about 250 ft. per minute. Based on this uncoiling rate, and an assumed weight of 0.026 pounds per foot for ⅜ inch diameter rope, the instantaneous throughput would be 13 lbs. per minute or 875,000 lbs. per year.

Each of the ropes 16, 18 is fed to an idler compensating unit 22 comprised of two non-driven idler rolls 24, 26, the first idler roll 24 being a single groove design and the second idler roll 26 being a double groove design. Leading into each idler roll 24, 26 is a UMHW PE oblong funnel 28 to direct the rope 16, 18 into the groove and to compensate for the change in side-to-side angle as the rope pays off the spool 12, 14. There is also a non-driven, hold down roll 30 above each idler roll 24, 26 to keep the rope captive in the idler roll groove. A spring loaded tensioning roll 32 is provided for each roll. This tensioning roll 32 will control the mechanical braking mechanism described above.

The ropes 16, 18 are next fed into an uncoiling and tensioning unit 34 comprised of an upper roll 36 and a lower roll 38, each formed with two grooves and both rolls driven by a single variable frequency controlled drive motor. This unit 34 controls the feed rate of the overall system. A non-driven, hold down roll 40 is provided for each driven roll 36, 38. The ropes 16, 18 then pass into a slack control unit 42 including a series of top fixed, non-driven, two grooved rolls 44 and a plurality of lower floating rolls 46 that move up and down depending on the relative feed rates of the uncoiling and tensioning unit 34 and a downstream cutter pinch roll feed unit 48. The vertical portion of the floating rolls 46 is sensed and the feed rate of the uncoiling end tensioning unit 34 is slightly adjusted to maintain the position of the floating rolls 46 and provide the pinch roll feed unit 48 with a constant rope tension and feed rate. When the ropes 16, 18 are initially fed through the slack control unit 42, the floating rolls 46 will rise to a position above the fixed rolls 44 to allow the operator to feed the two ropes across the tops of the fixed rolls 44 and into the downstream unit 48.

The ropes 16, 18 exiting the slack control unit 42 enter the cutter pinch roll feed unit 48 which is formed from a knurled-driven roll 50 and a pressure pinch roll 52. The speed of the driven roll 50 is controlled by a variable frequency drive unit to regulate the feed rate of the ropes 16, 18 into the cutter. The pinch roll 52 is forced against the knurled roll 50 by an air cylinder 54, and the pressure on the ropes 16, 18 at the bite point is controlled by air pressure. For initial feeding of the rope 16, 18, the air cylinder 54 and pinch roll 52 are retracted. The driven roll speed is slowed to the speed of the uncoiling and tensioning unit 34 for any major speed changes.

Ropes 16, 18 from the pinch roll feed unit 48 enter an inline cutter 56 having a rotary blade and six knives, a bed knife, a two-twenty horse power motor and a custom feed tube with six 6 ¾ diameter feed tubes. The cutter motor is controlled by a variable frequency drive unit. The rotary speed of the cutter 56 and the lineal feed rate of the pinch roll feed unit 48 determines the cut length of the fibers which is typically ¼ inch. There is a flex transition from the discharge of the cutter 56 into the suction feed tube of an air jet mill 58 and an integral dynamic classifier 60 where the irradiated rope pieces are micronized.

A control panel 62 is included in the system 10 to house disconnect breakers, a transformer, the three variable frequency drive units, a PLC with I/O modules and operator push buttons, selector switches and indicating lights. The panel further includes two start stop jog stations for use during initial threading of the rope 16, 18 through the system 10.

It should be understood that all tensioning equipment and the rope handling system 10 is used to compensate for the degradability of the rope fiber incurred during irradiation. The tensioning of the rope 16, 18 is typically between 5 and 50 pounds from the beginning of the system 10 to the end of the system 10.

Within some industries there are an applications that require acidity testing. This testing is mostly done in distilled water, by adding a powdered material such as cotton @ 1 to 10% levels with mild mixing and than taking pH reading.

It has been discovered that after Irradiation of the roped cotton, it leaves a residue on the fiber that registers a pH between 1.0 and 4.0. In order to sell product to applications that need it to be 7.0, a washing process must be included.

After micronization, the powdered cotton is than put through a washing and drying process as follows:

Material is put into a stainless steel vessel with either deionized or well water @ 50% levels. A mild cleaning surfactant is added @ 0.5 to 2.0% depending on pH levels and agitated for 10 to 20 minutes. Once agitated material is than sent to an air-drying system; where particles are airborne and introduced to warm airflow. Material is then discharged and tested for pH levels.

Various alternatives and embodiments are contemplated as being within the scope of the following claims particularly pointing out and distinctly claiming the subject matter regarded as the invention.

I claim:

1. In a method for preparing a multi-functional additive involving irradiating raw cotton plant material with an electron beam source, continually blending the raw cotton plant material during the irradiating and micronizing the irradiated cotton plant material, the improvement wherein:

the irradiating and blending of the raw cotton plant material is performed while the raw cotton plant material is in rope form; and the irradiated rope is suitably tensioned before micronizing to compensate for degradability of the rope incurred during irradiation.

2. The improvement of claim 1, wherein the irradiated rope is placed on at least one spool.

3. The improvement of claim 2, wherein the irradiated rope is fed to a roller and tensioning arrangement and a cutter before being micronized.

4. The improvement of claim 1, wherein after micronizing, the irradiated rope in powdered form is washed with a cleaning surfactant, agitated and dried so that the powdered cotton has a pH of 7.0.

5. A rope handling system for preparing a multi-functional additive from a raw cotton plant material comprising:

at least one spool of irradiated rope formed from the raw cotton plant material;

a roller and tensioning structure for receiving the irradiated rope from the spool;

a cutter connected to the roller and tensioning structure for chopping the irradiated rope to a predetermined size; and a micronizing structure connected to the cutter for reducing the chopped irradiated rope to a reduced size.

6. The rope handling system of claim 5, wherein after passing through the micronizing structure, the irradiated rope in powdered form is washed, agitated and dried so that the powdered cotton has a pH of 7.0.

7. A rope handling system for preparing a multi-functional additive from a raw cotton plant material comprising:

a pair of non-driven spools of irradiated rope formed from the raw cotton plant material;

an idler compensating unit for receiving the ropes from the spools;

an uncoiling and tensioning unit for receiving the ropes from the idler compensating units;

a slack control unit for receiving the ropes from the uncoiling and tensioning unit;

a cutter pinch roll feed unit for receiving ropes from the slack control unit;

an inline cutter for receiving and cutting the ropes from the pinch roller feed unit; and a control unit for regulating the operation of the idler compensating unit, the uncoiling and tensioning unit, the slack control unit, the cutter pinch roll feed unit and the inline cutter;

whereby the idler compensating unit compensates for the change in side to side angle as the ropes pay off the spools, the uncoiling and tensioning unit controls the feed rate of the overall system, and the slack control unit provides a constant rope tension and feed rate of the ropes into the pinch roll feed unit.

8. The rope handling system of claim 7, wherein the idler compensating unit includes a pair of non-driven, first idler rolls, a non-driven second idler roll above each first idler roll to keep the ropes captive in the grooves of the idler rolls, and a spring loaded tension roll for each rope.

9. The rope handling system of claim 7, wherein the uncoiling and tensioning unit includes an upper roll and a lower roll, both driven by a single, variable frequency controlled drive motor, there being a non-driven, hold down roll associated with each upper roll and lower roll.

10. The rope handling system of claim 7, wherein the slack control unit includes a series of upper, fixed, non-driven rolls and a set of floating lower rolls which move up and down according to the feed rates of the uncoiling and tensioning unit and the pinch roll feed unit.

11. The rope handling system of claim 7, wherein the cutter pinch roll feed unit includes a knurled driven roll and a pressure pinch roll associated with an air cylinder for forcing the pinch roll against the knurled driven roll.

12. The rope handling system of claim 7, wherein the rotary speed of the cutter and the lineal feed rate of the pinch roll feed unit determine the cut length of the irradiated rope fibers.

* * * * *